United States Patent
Thomson et al.

(10) Patent No.: US 9,449,149 B2
(45) Date of Patent: Sep. 20, 2016

(54) METHOD FOR OPTIMISING LOCAL DRUG DELIVERY

(75) Inventors: Rowena Thomson, Kirchheim (AU); Stephan Mittermeyer, Landshut (DE)

(73) Assignee: Brainlab AG, Feldkirchen (DE)

( * ) Notice: Subject to any disclaimer, the term of this patent is extended or adjusted under 35 U.S.C. 154(b) by 367 days.

(21) Appl. No.: 14/113,308

(22) PCT Filed: May 11, 2011

(86) PCT No.: PCT/EP2011/057618
§ 371 (c)(1),
(2), (4) Date: Oct. 22, 2013

(87) PCT Pub. No.: WO2012/152322
PCT Pub. Date: Nov. 15, 2012

(65) Prior Publication Data
US 2014/0058747 A1    Feb. 27, 2014

(51) Int. Cl.
*G06K 9/00*    (2006.01)
*G06F 19/00*    (2011.01)
*A61B 5/05*    (2006.01)

(52) U.S. Cl.
CPC ......... *G06F 19/3468* (2013.01); *G06F 19/345* (2013.01)

(58) Field of Classification Search
USPC ....... 382/100, 103, 106, 128–134, 154, 162, 382/168, 173, 181, 199, 219, 232, 254, 382/274–276, 285–291, 305, 312; 600/411, 600/561, 420; 604/116; 607/45; 378/4, 21
See application file for complete search history.

(56) References Cited

U.S. PATENT DOCUMENTS

| | | | | |
|---|---|---|---|---|
| 7,505,807 B1 * | 3/2009 | Kucharczyk | ....... | A61B 5/14525 600/411 |
| 7,742,630 B2 * | 6/2010 | Hartlep | ................... | A61M 5/14 382/128 |
| 2008/0082048 A1 * | 4/2008 | Ponce | ................... | A61M 5/172 604/116 |
| 2009/0024181 A1 * | 1/2009 | Raghavan | .............. | A61B 19/00 607/45 |
| 2009/0024418 A1 * | 1/2009 | Yu | ......................... | G06F 17/243 705/3 |
| 2009/0270712 A1 | 10/2009 | Raghavan et al. | | |
| 2010/0030102 A1 * | 2/2010 | Poston | ............... | A61B 17/3401 600/561 |
| 2010/0240986 A1 | 9/2010 | Stiles | | |

OTHER PUBLICATIONS

International Search Report for International Application No. PCT/EP2011/057618 dated Jun. 15, 2011.

* cited by examiner

*Primary Examiner* — Seyed Azarian
(74) *Attorney, Agent, or Firm* — Tucker Ellis LLP

(57) ABSTRACT

The present invention relates to a data processing method for determining an infusion location in an anatomical region of interest of a patient's body for infusing a medical substance, the method being executed by a computer and comprising steps of: a) acquiring permeability data comprising information about the permeability of anatomical vessels in the body; b) acquiring body vessels set data comprising information about a body vessel set, wherein the body vessel set represents a set of at least one anatomical body vessel in the patient's body and wherein the body vessel set data comprises information about the spatial structure of the at least one body vessel; c) acquiring coverage condition data comprising information about a predetermined coverage of a target region with the medical substance; d) determining, for a plurality of candidate infusion locations, candidate coverage data comprising information about a candidate coverage of a target region with the medical substance based on the permeability data, the body vessel set data and the coverage condition data; e) determining infusion location data comprising information about the infusion location based on the permeability data, the body vessel set data and the coverage condition data.

14 Claims, 3 Drawing Sheets

METHOD FOR OPTIMISING LOCAL DRUG DELIVERY

Figure 1A:
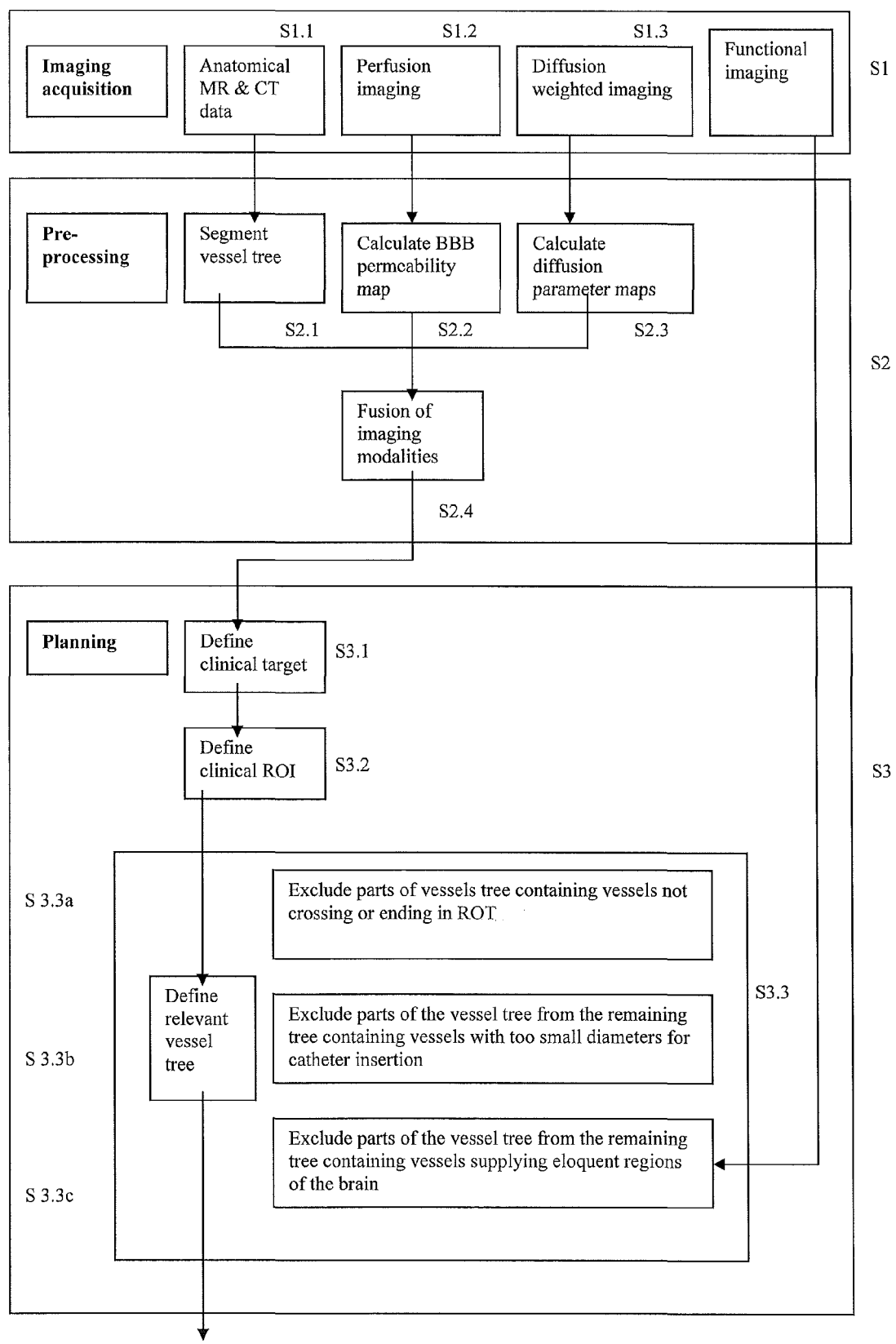

This application is a national phase of International Application No. PCT/EP2011/057618 filed May 11, 2011 and published in the English language.

The present invention is directed to a method, in particular a data processing method, for determining an infusion location in an anatomical region of interest of a patient's body for infusing a medical substance. The method is also directed to a corresponding computer program and a computer which runs the program as well as a navigation system using the information determined by the inventive method.

For brain tumours or neurodegenerative diseases, a treatment by delivery of chemotherapeutic agents is often preferred. Such delivery is commonly implemented by infusion of the agent into the blood stream. However, most of the currently applied therapeutic agents may be prevented by the blood-brain-barrier (BBB) from reaching the tumour or diseased tissue.

Currently, drug delivery catheters are placed within vessels under control of 3D-angiography without taking into account effects of the blood-brain-barrier which hamper transport of the agent to the tumour or diseased tissue.

Bullitt et al., Computerized assessment of vessel morphological changes during treatment of glioblastoma multiforme: Report of a case imaged serially by MRA over four years, NeuroImage 47 (2009) T143-T151, teach to select vessel segments used as an infusion location based on their tortuosity which is a measure for their inflection determined by summing the angles between consecutive points along a space curve, the sum being elevated at the presence of high-frequency, low-amplitude vessel sine waves or coils.

A problem to be solved by the invention is to improve the delivery of a medical substance to a target region.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The inventive method is in particular a data processing method, more particularly image data processing method for determining an infusion location in an anatomical region of interest of a patient's body for infusing a medical substance. The medical substance is preferably a contrast agent or a therapeutic agent (commonly also called drug), in particular a dispension, more particularly a suspension of a solid substance in a fluid or a solution of different fluids in one another. The medical substance is used for treating a disease, in particular a tumour or neurodegenerative disease. The tumour tissue or diseased tissue is preferably situated in the patient's brain or at another location, in particular in or near the central nervous system, which is by its nature protected by the blood-brain-barrier or a comparable anatomical feature preventing or hampering the propagation of fluid-based substances through biological tissue in particular based on substance-selective permeability (such as for example the placenta). The infusion location preferably is the location in the patient's body at which the medical substance leaves the instrument which is used for introducing it into the body, i.e. the infusion instrument. For example, the infusion location may coincide with the position of an open tip of a catheter placed inside the body, which catheter is designed for discharging the medical substance. The region of interest preferably comprises a target region which represents an anatomic region which is to be treated by infusing the medical substance and in particular comprises a clinical target such as a tumour or diseased tissue. The region of interest further comprises other, in particular healthy tissue and/or organs such as for example blood vessels or other hollow organs. The region of interest is a geometric region defined in the patient's body around the target region, in particular based on knowledge of the identity of the clinical target (i.e. describing which body region belongs to the target region and preferably its position in the body) and preferably its position in the body.

The inventive data processing method is preferably performed using technical means, in particular a computer. In particular, the data processing method is executed by or on a computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

Preferably, permeability data comprising information about the permeability of anatomical vessels in the body, in particular blood vessels, is acquired. In particular, the permeability data comprises information about the permeability of the vessel walls (more particularly, of the endothelium), more particularly of the permeability for the specific medical substance to be infused.

The expression "acquiring data" encompasses in particular (within the framework of a data processing method) the scenario in which the data are determined by the data processing method or program. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. The acquiring step in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe. The data acquired or determined by the inventive method may contain information described in two spatial dimensions or three spatial dimensions.

Preferably, the permeability data is acquired from medical image data, in particular from medical image which is or has been generated by using a perfusion imaging method.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernable in the image generated by the imaging method. In addition to these tumours, referred to as "enhancing" tumours, it is thought that approximately 10% of brain tumours are not discernable on a scan and are in particular not visible to a user looking at the images generated by the imaging method. MRI perfusion or CT perfusion imaging can provide information about blood flow, time to peek (delay from bolus to actual local distribution) and blood volume in a certain location. This allows to detect active parts of tumours or calculation of the permeability of the blood-brain-barrier.

For example, the permeability may be determined from the medical image data as suggested by Li et al., Simultaneous mapping of blood volume and endothelial permeability surface area product in gliomas using iterative analysis of first-pass dynamic contrast enhanced MRI data, The British Journal of Radiology, 76 (2003), 39-50. That publication teaches to use MR images to generate T2*W dynamic data to determine the concentration of a contrast agent in interstitial tissue which is proportional to the leakage profile multiplied with a volume transfer constant between blood plasma and interstitial tissue which is calculated from data collected during the first pass of the contrast agent bolus. Initial estimate of the tumour volume transfer constant between blood plasma and extravascular space is obtained by fitting the calculated leakage profile to the intravoxel concentration of contrast agent (the intravoxel concentration $C(t)$ being composed of an interstitial, i.e. extravascular, component $C_e(t)$ and an intravascular component $C_v(t)$, where $C(t)=C_e(t)+C_v(t)$). An initial estimate of the intravascular component can be obtained by subtracting the initial estimate of the interstitial component derived as described above from the intravoxel concentration. The volume transfer constant then is estimated by subtracting the contribution of recirculation of contrast agent through the intravascular compartment, which was calculated in the step of obtaining the initial estimate of the intravascular component, from the intravoxel concentration and refitting the resulting curve. The steps of obtaining the initial estimate of the intravascular component and estimating the volume transfer constant then are repeated in an iterative fashion to optimize the separation of intravascular and extravascular contrast agent effects. Voxel-by-voxel relative cerebral blood volume maps which have been corrected for the effects of contrast agent leakage into the interstitial space are then calculated from the integral over the intravascular concentration over time up to the time of the beginning of the recirculation phase identified from the plasma contrast concentration function which is a time course curve of the contrast agent concentration in plasma in large blood vessels.

Preferably, body vessel set data is acquired which comprises information about a body vessel set. The body vessel set preferably represents a set of at least one anatomical vessel, in particular blood vessel, in the patient's body. The set of anatomical vessels comprises at least one vessel. Such vessels are also termed body vessels. Body vessels preferably have no special relationship, in particular no predefined spatial relationship to the target region or region of interest. The information contained in the body vessel set data preferably comprise information about the anatomy of the patient's body, in particular the spatial structure, i.e. the geometry and position of the at least one vessel or at least one vessel tree in the patient's body. Preferably, the body vessel set data comprises information about the geometry of the body vessels. In particular, the body vessel set data comprises information about the diameter (or radius) and the path structure of the body vessels. More particularly, the information about the diameter is information about the inner diameter of the body vessels. The information about the path structure in particular encompasses information about the tortuosity of the vessels (as described above with regard to the publication by Bullitt et al.), the number of interconnected body vessels and whether the body vessels supply vital organs, in particular eloquent regions of the brain. In the context of this invention, a vessel tree denotes a set (in particular, a plurality) of preferably interconnected vessels. In particular, a vessel tree comprises a root vessel located upstream of all the other vessels which supplies all the other vessels with body fluid, in particular blood. All the other vessels preferably branch off the root vessel or are lower-generation vessels branching off vessels which directly branch off the root vessel. The farer a vessel is located from the root vessel, the smaller its diameter in general gets. Preferably, the body vessel set data is acquired by segmenting medical image data which has been generated by using an MR or CT imaging method. Preferably, relevant vessel set data is determined based on the body vessel set data.

Preferably, coverage condition data is acquired comprising information about a predetermined, in particular desired coverage of the target region with the medical substance. The term of coverage encompasses in particular the spatial distribution and the concentration of the medical substance in the target region. The predetermined, in particular desired value of coverage is preferably selected such that the coverage is sufficient for a successful treatment of the target region, in particular any pathologic state present in the target region, with a medical substance.

Preferably, candidate infusion locations are determined for the at least one body vessel. In particular, the candidate infusion locations correspond to possible infusion locations. This preferable plurality of possible infusion locations may be situated in one body vessel or different body vessels. The candidate infusion locations are determined based on preferably the position of the body vessel or body vessels in which they are situated relative to the region of interest and preferably based on the body vessel set data, more particularly on the information about the geometry of the body vessels contained in the body vessel set data. The candidate infusion locations represent a plurality of locations in body vessels which are suitable to conduct the envisaged treatment. The candidate coverage data comprises information about a determined coverage of the target region with a medical substance, in particular determined under the assumption of infusion of the medical substance at a specific candidate infusion location. For determining the candidate coverage, the permeability data is used in order to determine diffusion of the medical substance from the specific body vessel to the target region.

Preferably, the information about the candidate coverage contained in the candidate coverage data is compared to the information about the predetermined coverage contained in the coverage condition data. Preferably, this comparison comprises the evaluation whether the candidate coverage reaches the desired coverage or, in particular, lies within a predetermined interval below and/or above the predetermined coverage. This comparison is preferably conducted for the candidate coverage determined for each candidate infusion location. If the predetermined condition for the candidate coverage with regard to the predetermined coverage is not fulfilled, the method preferably continues with comparing a next value of candidate coverage with the predetermined coverage.

Preferably, a relevant vessel set is determined from the body vessel set based on the position of vessels contained in the body vessel set relative to the target region, in particular their distance from the target region and on the fact whether other, in particular vital, organs are located in-between the vessel set and the target region. Preferably, a body vessel contained in the body vessel set is determined to be part of the relevant vessel set (i.e. to be a relevant vessel) if it is close to the target region compared to other vessels in the body vessel set, in particular closer to the target region than other body vessels. The relevant vessel set therefore preferably constitutes a choice from a plurality of body vessels or vessel trees which are described by information contained in the body vessel set data. Preferably, the vessels contained in the relevant vessel set are determined such that they have a predetermined spatial relationship to the region of interest, in particular enter the region of interest, more particularly terminate in the region of interest or intersect the region of interest for a distance long enough to infuse the medical substance via the specific vessel into the region of interest.

Preferably, the relevant vessel set data comprises information about the geometry of the vessels contained in the relevant vessel set (i.e. the relevant vessels or vessel trees). In particular, the relevant vessel set data comprises information about the diameter (or radius) and the path structure of the relevant vessels. More particularly, the information about the diameter is information about the inner diameter of the relevant vessels. The information about the path structure in particular encompasses information about the tortuosity of the relevant vessels (as described above with regard to the publication by Bullitt et al.), the number of interconnected relevant vessels and whether the relevant vessels supply vital organs, in particular eloquent regions of the brain.

Preferably, the relevant vessel set data is determined based on fusion data, in particular image fusion data, which is determined preferably in a pre-processing block of data processing. The pre-processing block may be performed within or outside of the scope of the method according to the present invention. The fusion data is in particular determined by fusing body vessel data which has been preferably segmented from anatomical magnetic resonance and/or computer tomography data, permeability data comprising information about a permeability map of the blood-brain-barrier which preferably has been determined from perfusion imaging data, and diffusion parameter data describing at least one map of diffusion parameters of tissue in the patient's body which preferably has been determined from diffusion-weighted imaging data. In particular, the permeability of the body vessels serves as a boundary condition for determining the relevant vessel set. More particularly, the relevant vessel set is chosen such that the permeability of the vessels in the relevant vessel set suits the needs of the intended treatment and/or intervention on the patient. Thereby, the number of vessels or vessel trees which are determined to be potentially suitable to the geometry is reduced to those vessels or vessel trees which are suitable according to both their geometry and permeability, in particular permeability for the medical substance to be infused.

Image fusion, in particular image fusion transformations is/are in particular designed to enable a seamless transition from one image to another. The transformation is in particular designed such that one of the first and second images is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than 1/10 or 1/100 or 1/1000 of the diameter of the image, and in particular about equal to or less than the distance between neighbouring voxels. Due in particular to a high number of (iteration) steps, large deformations can be implemented.

The fusion data therefore preferably comprises information about the structure of body vessels, permeability of the vessels (in particular, permeability of the blood-brain-barrier) and the diffusion parameters which has been co-referenced. In particular, the values of permeability and diffusion parameters are referenced to spatial coordinates in the patient's body which are described in the same coordinate system as information about the position of the body vessels in the patient's body. If in the following disclosure, specific data is determined based on the fusion data, such specific data may be determined based on the body vessel set data, the permeability data or the diffusion parameter each by themselves or in combination. If the specific data is determined explicitly based on the body vessel set data and/or permeability data and/or diffusion parameter data, this specific data may be alternatively or additionally also determined based on the fusion data. The combination, in particular co-registration of the vessel structure data, permeability data and diffusion parameter data may alternatively be implemented by other algorithms than the above-described fusion algorithms as long as in particular the information contained in the data is transformed into a common coordinate system. The term of fusion data within the framework of this disclosure therefore does not only denote data which has been determined by image fusion but any kind of data which has been determined based on the vessel structure data, permeability data and diffusion parameter data wherein the information contained in them has been transformed into a common coordinate system.

Preferably, diffusion parameter data is acquired which comprises information about in particular diffusion parameters in tissue of the body. Preferably, the diffusion parameter data is generated from medical image data, in particular for medical image data which is or has been generated by using a diffusion-weighted imaging method. A preferred modality would be diffusion tensor imaging (DTI) which allows to calculate pressure maps of the tissue. DTI provides information about the probability distribution of directions a water molecule would travel within the tissue. This information can be used as a basis for estimating distribution of other fluids, like therapeutic agents, within the tissue.

The infusion location is preferably determined by determining infusion location data which comprises information, in particular spatial (more particularly, positional) information, about the infusion location. The infusion location data is preferably determined based on the permeability data, the body vessel set data, the coverage condition data and the candidate coverage data. In particular, the infusion location is selected from the group of candidate infusion locations. More particularly, the candidate infusion location for which the best candidate coverage has been determined is selected as the infusion location. The term of infusion location denotes the location in the patient's body at which infusion of the medical substance is determined to take place. In contrast thereto, the term of candidate infusion location denotes a location at which infusion of the medical substance is in regard of the envisaged treatment in principle possible and sensible, the candidate infusion location having to be evaluated whether it fulfils in particular the above-described criteria with regard to the candidate coverage in order to be eligible as an infusion location. The infusion location is preferably located in an infusion segment of a relevant vessel, wherein the infusion segment is a vessel segment in which discharge of the medical substance out of an infusion instrument such as a catheter takes place and through the walls of which the medical substance propagates, in particular permeates into the tissue surrounding the infusion segment and diffuses to the target region which preferably represents an anatomic region which is to be treated by infusing the medical substance. The information about the infusion location in particular describes the position of the infusion location, preferably its position in the relevant vessel (or, more generally, the patient's body). Alternatively or additionally, the infusion location data comprises information about the position of the infusion location relative to an insertion location of the infusion instrument such as the location of puncture at which a catheter is inserted into the patient's body. The infusion location data preferably comprises information about the position of the infusion location relative to other parts of the patient's body such as anatomical or artificial landmarks or internal organs.

Preferably, a user is offered a possibility for confirming or denying the selection of a candidate infusion location as infusion location. In case the user does not accept the determined infusion location, the method selects the candidate infusion location which fulfils in particular the conditions with regard to the candidate coverage second-best to the previously determined infusion location as a new infusion location. Preferably, the user is then again offered a possibility for acceptance or denying of that newly determined infusion location.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Other landmarks include a landmark defined by the rim of the acetabulum, for instance by the centre of the rim. In another example, a landmark represents the bottom or deepest point of an acetabulum, which is derived from a multitude of detection points. A detection point is in particular a point on the surface of the anatomical structure which is detected, for example by a pointer. Thus, one landmark can in particular represent a multitude of detection points.

Landmarks may be determined or acquired by using a pointer. A pointer preferably is a rod which comprises one or more—advantageously, two—markers fastened to it and can be used to measure off individual co-ordinates, in particular spatial co-ordinates (i.e. three-dimensional co-ordinates), on a part of the body within the framework of a morphing method, wherein a user guides the pointer (in particular, a part of the pointer which has a defined and advantageously fixed location with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (in particular, the tip of the pointer) is in particular known. The surgical navigation system then enables the location (of the three-dimensional co-ordinates) to be assigned to a predetermined body structure, wherein the assignment can be made automatically or by user intervention.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur when moved relative to the acetabulum. For structures of the brain, the centre line of the brain or bony structures in the head may serve as a landmark.

Preferably, the infusion location data is determined based on the fusion data. In particular, the infusion location data is determined based on the relevant vessel set data and the permeability data. The infusion location is in particular determined such that the geometry of the relevant vessels described by the relevant vessel set data suits the geometry of the infusion instrument, in particular such that the inner diameter of the vessel comprising the infusion segment fits the outer diameter of the catheter and that the tortuosity of the vessels along the insertion path of the catheter suits the elastic properties, in particular the flexibility, of the catheter. Thereby, it is ensured that the catheter may actually be inserted into the patient's body through vessels up to the infusion location. Furthermore, the infusion location is preferably determined such that the permeability of the vessel, in particular the vessel walls, at the infusion location matches the needs of the envisaged treatment and preferably also the material properties, i.e. chemical and/or physical properties, of the medical substance. In particular, the permeability of the infusion segments, i.e. the permeability of the vessel, in particular vessel walls, at the position of the infusion segment, should allow preferably all components or at least the active ingredients of the medical substance to permeate through the vessel wall into the surrounding tissue in consideration of infusion and body pressure, extravascular tissue and vessel wall properties such as porosity and chemical conditions such as osmotic pressure between the intravascular fluid (in particular the fluid containing the medical substance) and the fluid constituents of the extravascular tissue. Diffusion of the medical substance into the extravascular tissue shall preferably also be possible within a predetermined time and preferably at a predefined diffusion rate (i.e. a predetermined amount, in particular volume, of the medical substance per unit time).

The material properties, i.e. physical and/or chemical properties, of the medical substance are preferably described by information contained in medical substance data. Preferably, the infusion location data is determined also based on the medical substance data. In particular, the physical and/or chemical properties of the medical substance may serve as a condition for determining the infusion location. More particularly, the infusion location is not only determined based on the information contained in the vessel set data and the permeability data but also in conjunction with information about the physical properties (such as the viscosity or specific weight or particle size) and/or chemical properties (such as the chemical composition or reactivity, in particular reactivity with body fluids or human tissue) of the medical substance, in particular of the active ingredients contained in the medical substance which in particular support a therapeutic effect of the medical substance. In particular, the infusion location is determined such that the material properties of the medical substance do not hamper the envisaged infusion therapy in consideration of the other conditions according to which the infusion location is determined.

Preferably, region of interest data comprising information about the region of interest is acquired. The region of interest data in particular comprises information about the position of the region of interest, in particular the position relative to the clinical target and/or target region. Alternatively or additionally, the region of interest data preferably also comprises information about the geometry (in particular, volume and/or shape, in particular a shape which may be described or approximated by basic geometric shapes such as a sphere, an ellipsoid or a box). For example, the region of interest data may comprise information about a spherical function or a vector-based function describing the position and preferably also the volume of the region of interest, in particular relative to the target region and/or the clinical target. The region of interest data is preferably acquired based on the fusion data. The region of interest which is described by the region of interest data is preferably determined based on the fusion data, in particular the permeability data and the body vessel set data as well as the diffusion parameter data such that the region of interest comprises the target region. Preferably, the relevant vessel set data is determined based on the region of interest data such that the relevant vessels have suitable geometry and permeability for inserting the infusion instrument and enabling infusion and such that the extravascular tissue surrounding a potential infusion segment of at least one vessel contained in the relevant vessel set is suitable to allow propagation of a medical substance (in particular, the medical substance which shall be infused during the envisaged treatment) to the target region. The region of interest data preferably serves as a selection from the fusion data which may in particular comprise plural possible candidates for an infusion location. From those plural candidates, a suitable infusion location may then be determined by, for example, an optimization algorithm which determines the most suitable infusion location among the candidates according to the conditions to be fulfilled by the infusion location.

Preferably, a body fluid volume in the infusion segment is determined. Preferably, also a concentration of the medical substance in the infusion segment after discharge from an infusion instrument is determined. Preferably, the infusion by discharge from an infusion instrument is performed by inserting a catheter, in particular a balloon catheter comprising two inflatable balloons proximal and distal to a releasing port of the catheter, into a blood vessel, in particular a relevant vessel. The catheter is then placed such that the inner boundaries of the balloons preferably form the outer boundaries of the infusion segment or at least both lie within the infusion segment. In particular, the releasing port is located at or as close as possible to the infusion location. The volume of the infusion segment may then be determined by for example the distance between the balloons and the inner radius (or diameter, respectively) of the infusion segment and using the approximation of a cylindrical infusion segment. The balloons are preferably inflatable balloons which are inflated after placing the catheter at the desired location in or at the infusion segment. Thereby, the blood vessel is at least temporarily (i.e. at least for the time of discharge of the medical substance and the time which the medical substance needs to permeate into the extravascular tissue) occluded proximally and distally of the position of the proximal and distal balloons. Alternatively, the infusion instrument is a flexible catheter comprising an expandable material, in particular along a major part or all of its longitudinal extension, which enables a tight fit with the innermost vessel wall, in particular the vessel wall at or immediately around the infusion location. This supports release of the medical substance from the infusion instrument at a discrete, spatially exact location in the vessel and avoids the necessity for determining a concentration of the medical substance in the infusion segment. In particular, the medical substance is discharged from the releasing port to only contact the innermost vessel wall right at the infusion location. Thereby, it is also avoided that the medical substance diffuses from the infusion location in an undesired direction.

The infusion segment preferably is located in a vein, may however alternatively be located in an artery. Therefore, the term of vessel, in particular blood vessel in the context of this invention encompasses both veins and arteries. A body fluid volume in the infusion segment may then be determined from a known or estimated body fluid, in particular blood, volume present between the inflated balloons. The concentration of the medical substance in the infusion segment is then preferably determined from information about a predetermined or known volume of medical substance which has been discharged to the infusion segment and the information about the body fluid volume in the infusion segment. In particular, the medical substance forms a solution or dispension, in particular suspension, with the body fluid volume. A concentration of the medical substance in the tissue immediately surrounding the vessel around the infusion segment is then preferably determined based on the permeability data, and preferably based on also on information about the concentration of the medical substance in the infusion segment. To this end, in particular information about the permeability of the infusion segment contained in the permeability data is used. The information about the concentration of the medical substance in the tissue surrounding the infusion segment preferably also serves as a basis for determining the infusion location, in particular for determining a preferred infusion location from plural candidates for potentially suitable infusion locations. In particular, the infusion location may be determined such that the determined concentration of the medical substance in the surrounding tissue fulfils a predetermined relationship to a predetermined threshold value of concentration, in particular is larger or equal than the threshold value.

Preferably, the diffusion of the medical substance in the tissue contained in the region of interest, in particular also in the target region, is determined based on the diffusion parameter data. Preferably, also coverage of the target region by the medical substance is determined. Determining the coverage of the target region by the medical substance in particular encompasses determining a concentration and/or a spatial distribution of the medical substance in the target region, in particular under the assumption of a predefined infusion location. However, the infusion location may also be determined based on information about the diffusion of the medical substance in the tissue contained in the region of interest and/or on information about the coverage of the target region. Thus, both a forward and a backward determination of the infusion location is within the scope of the invention.

It is to be noted that the infusion location data may be determined based on the relevant vessel set data, i.e. a candidate infusion location is evaluated whether it belongs to a relevant vessel (a relevant vessel tree) and, if this is the case, is determined to be the infusion location. Alternatively, the relevant vessel set data may be determined based on the infusion location data such that a check whether the body vessel (body vessel tree) in which a candidate infusion location is situated is eligible as a relevant vessel. If this is not the case, the candidate infusion location is preferably not determined to be the infusion location. Preferably, the inventive method then proceeds with evaluating another candidate infusion location in this manner. Thus, the order of method steps for determining the relevant vessel set data and the infusion location data is not fixed, in particular one data set may be determined based on the other and vice versa.

The invention also relates to a program which, when running on a computer or when loaded onto a computer, causes the computer to perform one or more of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The invention furthermore relates to a navigation system for navigating an infusion instrument comprising a computer configured to read the infusion location data determined by the above-described method and preferably to display information about the location of the infusion instrument, in particular on a display device (i.e. a visual indicating means) connected to the computer. The navigation system preferably comprises a detection device for detecting the position of the catheter, in particular by measuring the inserted catheter length and determining its position in the brain from for example information about the elastic properties of the catheter and a force applied to for example a guiding device of the catheter such as a handle used by an operator. A corresponding method and system is described in the applicant's European patent EP 1 925 265 B1 titled "Length determination of a flexible rod-shaped instrument", the contents of which is incorporated into the present disclosure by reference.

The navigation system acquires the infusion location data determined according to the above-described method and acquires information about the position of the infusion location data in the body and preferably compares this information to information about the present position of the infusion instrument, in particular of the discharge opening of the infusion instrument, when inserted into the patient's body. The navigation system preferably outputs visual and/or acoustic and/or tactile information to an operator if, for instance, the infusion instrument, in particular its discharge opening, has reached a predetermined relationship to the infusion location (in particular is coincident with the infusion location or deviates from the infusion location by a predetermined amount).

Figure 1B:
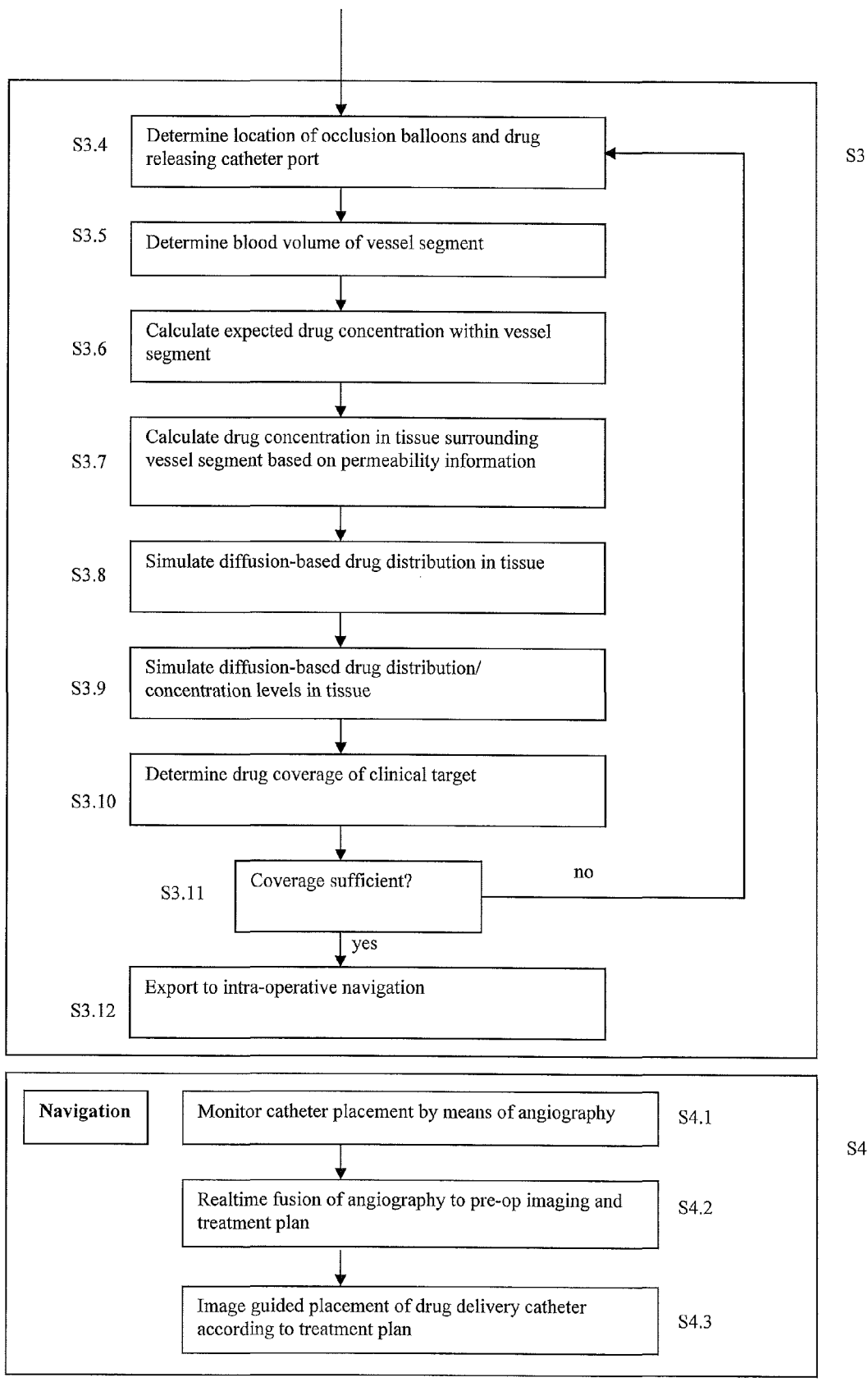
Figure 2:
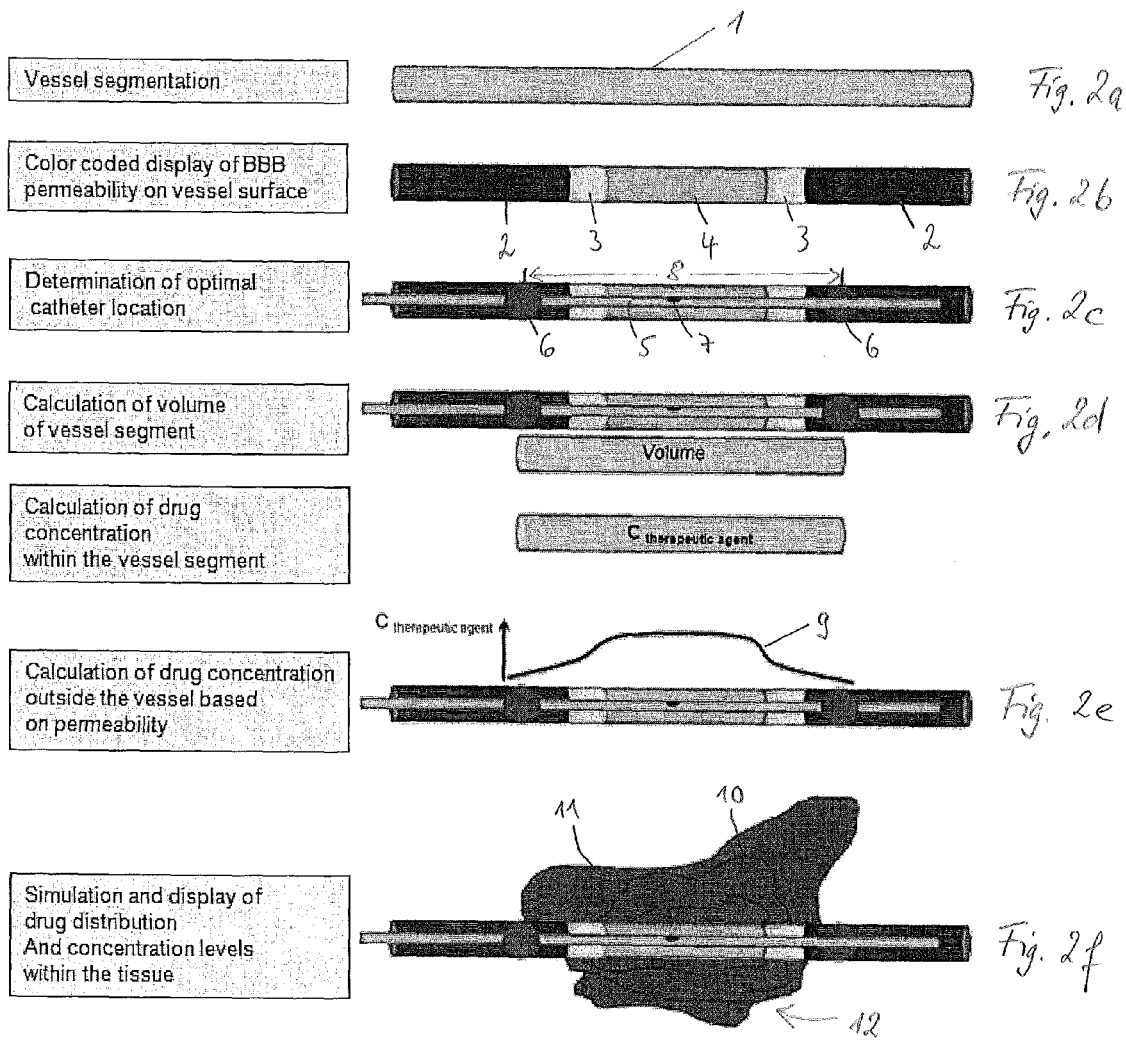

The invention is described below in more detail with reference to the figures which show exemplary embodiments of the present invention, wherein FIGS. 1a and 1b show a flow diagram of a method for determining an infusion location and navigating an infusion catheter;

FIG. 2 shows placement of an infusion catheter in an infusion segment.

FIGS. 1a and 1b show method blocks of imaging acquisition (i.e. acquisition of medical image data) S1, pre-processing of the medical image data S2, planning of the infusion treatment (comprising the steps of determining the infusion location) S3 and navigating an infusion instrument S4. The method step shown in FIGS. 1a and 1b are to be understood as a continuation of the method steps shown in FIG. 1.

Method block S1 represents acquiring the medical image data which in pre-processing block S2 is used to extract the information based on which the infusion location is determined S3. In step S1.1, anatomical image data is acquired by taking an MR or CT image of the patient's body. Based on the anatomical data, body vessel data is determined in step S2.1 by segmenting at least one vessel tree, preferably at least a plurality of vessels, from the anatomical data. To this end, the anatomical data comprises information, in particular image information, which allows to determine the geometry and position of the vessels (vessel tree) in the patient's body. For example, the plurality of vessels (the at least one vessel tree) is segmented based on a pattern recognition technique or on a colour value (in particular, a colour contrast value) described by the pixels or voxels used for discretizing the image information. In step S1.2, perfusion data comprising information about the permeability of tissue in the patient's body is acquired by performing a perfusion imaging technique. Based on the perfusion data, a permeability map of the blood-brain-barrier is calculated in step S2.2. Perfusion imaging is in particular performed as a scintigraphy of tissue in the patient's body which has been treated with a contrast agent. Based on the spread and concentration of the contrast agent in the tissue which may be determined based on colour values contained in the perfusion image data (in analogy to segmenting the vessels from the anatomical data), the permeability of tissue forming the blood-brain-barrier, in particular the endothelium of vessels, is calculated. To this end, the contrast agent preferably is a substance which is suitable for passing through the blood-brain-barrier.

In step S1.3, diffusion image data is acquired by performing diffusion imaging on the patient's body. The diffusion image data comprises information about the diffusion properties of tissue in the patient's body. Diffusion imaging is a magnetic resonance imaging (MR or MM) method that produces in vivo images of biological tissue weighted with local microstructural characteristics of water diffusion. Within the framework of this invention, the diffusion imaging may be diffusion weighted imaging (DWI) or diffusion tensor imaging (DTI). In DWI, each image voxel has an image intensity that reflects a single best measurement of the rate of water diffusion at that location. DWI is applicable in particular when the tissue of interest is dominated by isotropic water movement, for example the gray matter in the cerebral cortex and major brain nuclei. DTI is used in particular when a tissue—such as the neuro axons of white brain matter or muscle fibers in the heart—has an internal fibrous structure analogous to the anisotropy of some crystals. In some cases, water diffuses more rapidly in a direction aligned with the internal structure, and more slowly as it moves perpendicular to that direction which also termed a preferred direction. The diffusion parameter maps calculated in step S2.3 comprise information about the spatial distribution of diffusion parameters in the tissue of the patient's body.

In step S2.4, the body vessel data, the permeability data and diffusion parameter data are fused into fusion data. Thereby, the spatial information contained in the body vessel data, permeability data and diffusion parameter data is transformed into a common coordinate system.

Block S3 represents the flow of planning the infusion and in particular determining the infusion location. The planning S3 is performed based on the results of the pre-processing S2. In particular, the fusion data determined in step S2.4 is used as a basis, in particular as input data, for the planning S3. In step S3.1, the clinical target, i.e. the target region, is defined. Preferably, the definition is performed as user interaction on a graphic display of the fusion data. For example, a user may execute a marking operation by using a mouse or comparable pointer device for marking the clinical target in the fusion data which is displayed on a display device such as a monitor. In the following step S3.2, the clinical region of interest (ROI) is defined. This is again preferably performed as a user interaction such as defining the clinical target. In particular, the user defines an area or volume around the clinical target. The region of interest is then described by the above-mentioned region of interest data. Preferably, the region of interest is defined such that a plurality of vessels or vessel trees which are potentially suitable for performing the infusion are located in the region of interest. This is supported by the information contents of the fusion data since the fusion data comprises information about the position of the body vessels in the patient's body.

In step S3.3, the relevant vessel tree or relevant vessels is or are determined. To this end, step S3.3 comprises a number of sub-steps S3.3a to S3.3c. These steps are preferably performed automatically based on known image data processing techniques, in particular pattern or colour value recognition, and alternatively or additionally on evaluating the position of certain anatomical structures (such as vessels or vessel trees) with regard to the position of other anatomical structures (such as eloquent regions of the brain) or other predetermined data such as data comprising information about the geometry and/or elastic properties of the infusion catheter. In step S3.3a, parts of vessels or vessel trees containing vessels which do not enter the region of interest, in particular do not cross (intersect) or end in the region of interest, are excluded from the vessels or vessel trees described by the information contained in the body vessel data. Therefore, a first selection of vessels or vessel trees based on their position with respect to the region of interest is determined from the plurality of vessels or vessel trees described by the information in the body vessel data. In the following step S3.3b, parts of vessels or vessel trees are excluded from the vessels or vessel trees determined in step S3.3a if their geometry (in particular diameter or tortuosity) is not suitable for inserting the infusion catheter, in particular if the inner diameter of the vessels is too small with regard to the outer diameter of the infusion catheter or if their tortuosity is too large with regard to the flexibility of the infusion catheter. Preferably, step S3.3 also comprises step S3.3c in which, from the vessels or vessel trees determined in step S3.3b, those vessels or vessel trees or their parts, respectively, are excluded which supply eloquent regions of the brain with body fluids such as blood. Among other reasons, this helps to avoid infusing aggressive medical substances to brain regions which are vital and shall not be influenced by the effects of the medical substance. Information about the position of eloquent regions in the brain with regard to the vessel or vessel tree is preferably gathered by acquiring functional imaging data of the patient's brain. Functional imaging in particular is performed by acquiring functional magnetic resonance imaging data (fMRI data) of the patient's brain which measures the haemodynamic response (i.e. change in blood flow related to neuroactivity in the brain or other parts of their central nervous system such as the spinal cord of the patient). Alternatively or additionally, the functional imaging data may be acquired by using any other neuroimaging modality such as a computed axial tomography (CAT) or diffuse optical imaging (DOI). The functional imaging data then is preferably fused with the fusion data or fused with the body vessel data, the permeability data and the diffusion parameter data to form the fusion data. In particular, the spatial information in the functional imaging data is mapped into the same coordinate system as the other data sets.

After performing the exclusion steps on body vessels contained in the region of interest as described by S3.3, a relevant vessel or relevant vessel tree remains which is in particular automatically determined as comprising an infusion segment and therefore being suitable for performing the infusion treatment.

In step S3.4, the location of the occlusion balloons and the drug releasing port of the infusion catheter for performing the infusion and therefore the position of the infusion segments and the infusion location in the relevant vessel or relevant vessel tree is determined. To this end, in particular data about the geometry of the infusion catheter, more particularly the position of the occlusion balloons and the drug releasing port in the infusion catheter, is combined with information about the position of the relevant vessel or relevant vessel tree. In step S3.5, the blood volume in the infusion segment determined in step S3.4 is calculated as described above. In step S3.6, the expected drug concentration within the infusion segment is calculated as explained above. In step S3.7, an expected concentration of the drug in the interstitial tissue surrounding the infusion segment is determined based on the permeability information derived from the permeability data.

The propagation, in particular diffusion of the medical substance into the interstitial tissue, in particular the tissue located in the target region and in-between the infusion segment and the target region, is simulated based on the information about the diffusion properties of tissue in the patient's body contained in the diffusion parameter data. Based on the information about the diffusion of the medical substance in the interstitial tissue, in particular when combined with information about the time necessary for reaching certain stages of diffusion in step S3.8, the concentration of the medical substance in the tissue is determined in step S3.9. Similarly, spatial coverage of the clinical target by the medical substance and concentration of the medical substance in the target region is determined in step S3.10.

In step S3.11 it is evaluated whether the spatial coverage and concentration of the medical substance in the target region is sufficient by comparing the results of step S3.10 with corresponding predetermined data comprising information about a desired spatial coverage and concentration of the medical substance in the target region. If it is evaluated that the spatial coverage and concentration is not sufficient in order to reach the desired treatment results, the method reverts to step S3.4 and repeats the following steps for another relevant vessel or relevant vessel tree. To this end, preferably a plurality of relevant vessels or relevant vessel trees is determined in step S3.3 and preferably also ordered such that for each iteration of steps S3.4 to S3.11, the relevant vessels or relevant vessel trees are used as a basis for determining the infusion location in order of descending suitability of the relevant vessels or relevant vessel trees for the envisaged treatment.

If step S3.11 determines that the spatial coverage and concentration of the medical substance in the target region are sufficient, the infusion location data is determined in step S3.12. The infusion location data comprises information about the position of the infusion segments in the patient's body and preferably about the permeability characteristics of the infusion segment as well as the diffusion properties of the tissue in the target region and the region of interest (in particular, between the infusion segment and the target region). Preferably, the infusion location data is readable for a navigation system in order to support intra-operative navigation of the infusion catheter.

Block S4 comprises steps of navigating the infusion instrument during the operation (treatment). Navigation is preferably performed based on the infusion location data determined in block S3. In step S4.1, a method of angiography is used to monitor the position of the infusion catheter in the patient's body. Thereby, angiography data comprising corresponding information is determined. The angiography data is in step S4.2 fused to the infusion location data. The fused angiography data and infusion location data are used in step S4.3 to support visual navigation by means of image-guided infusion catheter placement, in particular in accordance with a predetermined treatment plan.

FIG. 2 shows placement of an infusion catheter 4 in a relevant vessel 1. FIG. 2a is a depiction of a relevant vessel 1 approximated as an elongated cylinder which is segmented from the body vessel data. FIG. 2b shows colour-coded display (represented in greyscales) of the blood-brain-barrier determined based on the permeability information for the walls of relevant vessel 1. Dark-coloured regions 2 represent parts of the relevant vessel 1 which are not suitable as an infusion segment, whereas light-shaded regions 3 represent parts of relevant vessel 1 having a higher permeability than regions 2. In the centre between regions 3, medium-shaded region 4 corresponding to a most suitable part of relevant vessel 1 for performing the infusion is visualized. In accordance with FIG. 2c, the optimal placement of the infusion catheter 5 is determined by placing the occlusion balloons 6 through which catheter 5 runs in regions 2 close to the outer boundaries of regions 3. Preferably, the drug releasing port 7 of catheter 5 is located in the centre between occlusion balloon 6 and therefore in the centre of region 4. The longitudinal section of relevant vessel 1 located in-between the vessel wall parts which touch the occlusion balloons 6 defines the infusion segment 8.

According to FIG. 2d, the volume of the infusion segment 7 and the concentration of the medical substance $C_{therapeutic\ agent}$ is determined as described above. The concentration of the medical substance in the interstitial tissue surrounding the infusion segment then is determined based on the permeability of the infusion segment as described by FIG. 2e. The curve 9 shown in FIG. 2e depicts the concentration of the medical substance as a function of position along the infusion segment 8. Thereby, it becomes clear that the highest concentration is achieved along the longitudinal extension of region 4 and decreases towards the outer ends of the infusion segment 8. In particular, the boundary from a low concentration of medical substance to an acceptable concentration lies around the boundary between regions 3 and 4.

FIG. 2f shows graphical determination of diffusion of the medical substance based on the concentration of the medical substance in the interstitial tissue and the diffusion properties of the interstitial tissue. The shaded surface on both sides of the infusion segment 8 explains the spread 11 of medical substance in the surrounding tissue, where in different levels of concentration of the medical substance in the tissue may be visualized by areas of different colour shade separated by contour lines 7. Preferably, the spread of the medical substance in the interstitial tissue is also determined for tissue which lies on the averted side of the infusion segment, in particular tissue which does not lie in-between the infusion segment and the target region. Thus, it may also be determined how much of the medical substance permeates into tissue which is not relevant for the envisaged treatment.

The invention claimed is:

1. A data processing method for determining an infusion location in an anatomical region of interest of an associated patient's body for infusing a medical substance, the method being executed by a computer and comprising steps of:
   a) acquiring permeability data comprising information about the permeability of anatomical vessels in the body;
   b) acquiring body vessel set data comprising information about a body vessel set, wherein the body vessel set represents a set of at least one anatomical body vessel in the associated patient's body and wherein the body vessel set data comprises information about the spatial structure of the at least one body vessel;

c) acquiring coverage condition data comprising information about a predetermined coverage of a target region with the medical substance;

d) determining, for a plurality of candidate infusion locations, candidate coverage data comprising information about a candidate coverage of the target region with the medical substance based on the permeability data, the body vessel set data and the coverage condition data;

e) determining infusion location data comprising information about the infusion location based on:
the permeability data,
the body vessel set data,
the candidate coverage data, and
the coverage condition data,
wherein the infusion location is located in an infusion segment of a vessel, and
wherein a body fluid volume in the infusion segment is determined and a concentration of the medical substance in the infusion segment is determined and wherein a concentration of the medical substance in the tissue surrounding the infusion segment is determined based on the permeability data.

2. The method according to claim 1, wherein the body vessel set data comprises information about the diameter and the path structure of the at least one body.

3. The method according to claim 1, further comprising a step of:
f) determining relevant vessel set data based on the body vessel set data, the relevant vessel set data comprising information about a relevant vessel set of relevant vessels.

4. The method according to claim 1, further comprising a step of:
g) acquiring target region data comprising information about a target region which represents an anatomical region which is to be treated by infusing the medical substance.

5. The method according to claim 1, wherein the permeability data is acquired based on medical image data.

6. The method according to claim 1, wherein the relevant vessel set data is determined based on the permeability data.

7. The method according to claim 1, wherein region of interest data comprising information about the region of interest is determined based on the permeability data, body vessel set data comprising information about the position of vessels in the body and diffusion parameter data comprising information about diffusion parameters in tissue of the body, wherein the diffusion parameter data is generated from medical image data.

8. The method according to claim 1, wherein the infusion location data is determined based on medical substance data comprising information about a material property of the medical substance.

9. The method according to claim 1, wherein the infusion location data comprises information about a plurality of infusion locations and wherein a preferred one of the infusion locations is determined based on the determined concentration of the medical substance in the tissue surrounding the infusion segment.

10. The method according to claim 9, wherein diffusion of the medical substance in the tissue contained in the region of interest is determined based on the diffusion parameter data and wherein coverage of the target region by the medical substance is determined.

11. The method according to claim 1, wherein the method is used for tumor treatment.

12. A non-transitory computer readable storage medium storing a program which, when running on a computer or when loaded onto a computer, causes the computer to perform a data processing method for determining an infusion location in an anatomical region of interest of an associated patient's body for infusing a medical substance, the method being executed by a computer and comprising steps of:

a) acquiring permeability data comprising information about the permeability of anatomical vessels in the body;

b) acquiring body vessel set data comprising information about a body vessel set, wherein the body vessel set represents a set of at least one anatomical body vessel in the associated patient's body and wherein the body vessel set data comprises information about the spatial structure of the at least one body vessel;

c) acquiring coverage condition data comprising information about a predetermined coverage of a target region with the medical substance;

d) determining, for a plurality of candidate infusion locations, candidate coverage data comprising information about a candidate coverage of the target region with the medical substance based on the permeability data, the body vessel set data and the coverage condition data;

e) determining infusion location data comprising information about the infusion location based on:
the permeability data,
the body vessel set data,
the candidate coverage data, and
the coverage condition data,
wherein the infusion location is located in an infusion segment of a vessel, and
wherein a body fluid volume in the infusion segment is determined and a concentration of the medical substance in the infusion segment is determined and wherein a concentration of the medical substance in the tissue surrounding the infusion segment is determined based on the permeability data.

13. A computer operably coupled to the non-transitory computer readable storage medium of claim 12.

14. A navigation system for navigating an infusion instrument comprising the computer of claim 13, the computer being configured to acquire the determined infusion location data and to display information about the location of the infusion instrument.

* * * * *